United States Patent
Cheon et al.

(12) 
(10) Patent No.: US 6,465,020 B1
(45) Date of Patent: Oct. 15, 2002

(54) USE OF GARLIC EXTRACT AS BOTH PREVENTIVE AND THERAPEUTIC AGENTS FOR HUMAN PROSTATE AND BLADDER CANCERS

(75) Inventors: Jun Cheon; Jejong Kim; Jungku Lee; Hankyeum Kim; Doogun Moon, all of Seoul (KR)

(73) Assignee: Korea Chungang Educational Foundation, Seoul (KR)

( * ) Notice: Subject to any disclaimer, the term of this patent is extended or adjusted under 35 U.S.C. 154(b) by 11 days.

(21) Appl. No.: 09/610,322

(22) Filed: Jul. 5, 2000

(51) Int. Cl.$^7$ .................. A61K 35/78; A61K 31/255
(52) U.S. Cl. ........................ 424/754; 514/517
(58) Field of Search ........................ 514/517; 424/754

(56) References Cited

PUBLICATIONS

Nakata, Nippon Eiseigaku Zasshi, 27(6), 538–43 Abstract Only, 1973.*

Cheng et al., T'ai–wan I Hsueh Hui Tsa Chih, 80(4), 385–93 Abstract Only, 1981.*

Zheng et al., J. Cell. Biochem., Suppl. 27, 106–112, Abstract Only, 1998.*

Tsai et al., Planta Med., (5), pp 460–1 Abstract Only, 1986.*

Kim et al., Biosci. Biotechnol., Biochem., 61(9), pp 1482–1485 Abstract Only, 1997.*

* cited by examiner

*Primary Examiner*—Jerome D. Goldberg
(74) *Attorney, Agent, or Firm*—Morrison & Foerster LLP

(57) ABSTRACT

This invention is concerned with the clinical investigation of the therapeutic effects of garlic extracts containing allicin, diallyl disulfide, and diallyl trisulfide. The intake of garlic or therapeutically active substances such as allicin from garlic, induces immunostimulation and these active substances possess strong antitumor effects including the apoptosis of tumors, including the programmed cell death of human prostatic and bladder tumor cells. This invention claims that garlic and/or garlic extracts possess very effective therapeutic substances useful not only to treat human prostate and bladder cancers to extend life span of patients, but also to suppress or prevent bladder and prostate gland cancers.

3 Claims, 2 Drawing Sheets

A: × 100

B: × 400

A: × 200

B: × 400

USE OF GARLIC EXTRACT AS BOTH PREVENTIVE AND THERAPEUTIC AGENTS FOR HUMAN PROSTATE AND BLADDER CANCERS

BACKGROUND OF THE INVENTION

1. Field of the Invention

This invention is relates to new therapeutic applications of garlic extracts containing allicin, diallyl disulfide, trisulfide, etc., and more specifically this application relates to the use of these extracts against human prostate gland and bladder tumors. The therapeutic applications relate to the strong immunostimulation mediated anticancer effects elicited by allicin, diallyl disulfide, and diallyl trisulfide in garlic extracts, which induce programmed prostate and bladder cancer cell death.

2. Description of the Prior Art

Prostate cancer death is prevalent in the U.S. and Europe. Prostate cancer is the second largest cause of cancer death among the male population in these countries. In Korea, as the elderly male population increases and as more advanced diagnostic techniques for detecting prostate cancers are imported into the country, the incidence of detected prostate cancers within Korea is expected to increase. The incidence of prostate cancer within Korea is also expected to rise because of dramatic changes in dietary habits, including the increased consumption of dairy products, which are closely associated with the number of male prostate cancer patients and an increase in male mortality due to prostate cancer. Thus, prostate cancer in Korea is expected to become one of the major socially important diseases.

Unfortunately, when many patients are diagnosed with prostate cancer, prostate tumors have already metastasized to bone marrow and lymph nodes. In such cases, the only treatment mode is hormonal therapy (either radical orchiectomy of both testes and/or continued injection of LHRH analogues). Most patients respond well to primary treatment, however, more than half of the patients develop resistance to hormonal treatment and unfortunately, these patients die within a year to a year and a half. Consequently, it was very much desired to find new therapeutic regimens or ways to increase the quality of life for patients who are resistant to hormonal therapy. Effective new therapeutic regimens have not yet been discovered. Furthermore, the discovery of preventive therapeutic agents that significantly reduce the incidence of prostate cancer without serious side effects, will become highly desired.

The etiology of malignant bladder cancers are attributed to long term exposure to cigarette smoke and/or environmental carcinogens. In Korea, the incidence of bladder cancer is the highest among urinary and reproductive tract cancers and is one of the top five most prevalent types of cancers among males. Male bladder cancer incidence is expected to increase and likewise, the mortality rate is expected to increase. Bladder cancers are classified into 3 categories based on their progression. The three categories are superficial, invasive, and metastatic cancers. The incidence of superficial bladder cancer is the highest, but even if this category of bladder cancer is found at an early stage, resection of the urethra and bladder are required. Additionally, even if all visible tumors are removed by resection, the reoccurrence rate is still as high as 50~70%. Repeated resections lead to a higher incidence of complication such as urethra stricture, bladder perforation, and severe inflammation. In recent times, in attempt to reduce recurrence of bladder tumors, chemotherapeutic agents or immunomodulators are often prescribed following the initial tumor resection. Nonetheless, extremely bloody urine and inflammation of the urethra ensue, which further complicates treatment to stop the continued progression of bladder cancers. Furthermore, in the case of invasive bladder cancers, a radical resection of the bladder is required which requires the use of an artificial bladder. This causes not only severe disruption to the daily livelihood of patients, but also often leads to postsurgical complications.

When patients are diagnosed with metastasized bladder cancers, the only treatment left is to treat the patients with aggressive chemotherapy, but this leads to severe complications. Even with the use of aggressive chemotherapy, the prognosis of patients with metastasized bladder cancers is not very good. For this reason, it is of vital importance that more effective therapeutic agents or highly effective preventive agents for use against the occurrence of bladder cancers need to be developed. Especially, it is highly desirable to develop effective chemopreventive agents that do not have severe side effects or an unreasonable cost.

SUMMARY OF THE INVENTION

The inventors sought to find either therapeutic chemicals or the extracts of natural plants to provide new alternative therapeutic or preventive agents for the treatment of prostate and bladder cancer. Treatments that selectively eradicate both prostatic and bladder cancer cells were specifically sought. We were able to discover and complete this invention as a result of our experimental research showing that garlic extracts clearly possesses chemopreventive effects, and also that they induce programmed cancer cell death in both prostate and bladder cancer cells.

Furthermore, the objective of the invention is to propose that garlic extracts containing allicin are highly effective preventive and/or chemotherapeutic agents against prostatic and bladder cancers. The other objective of this invention is to show that compositions of garlic extracts containing allicin are very effective chemotherapeutic agents for use against prostatic and bladder cancers.

The object of the invention previously described is accomplished by experimentally confirming that garlic extracts containing allicin, diallyl disulfide, diallyl trisulfide, and inclusive of other effective compounds are highly effective chemopreventive and/or chemotheraputic agents in experimental mice bearing human prostatic and bladder tumors.

A chemopreventive and chemotherapeutic composition for human prostate and human bladder cancers comprising allicin-containing garlic extracts isolated and purified from garlic, is described in detail below.

BRIEF DESCRIPTION OF THE DRAWINGS

The above and other objects, features and other advantageous of the present invention will be more clearly understood from the following detailed description taken in conjunction with the accompanying drawings, in which.

DESCRIPTION OF THE PREFERRED EMBODIMENTS

Figure 1:
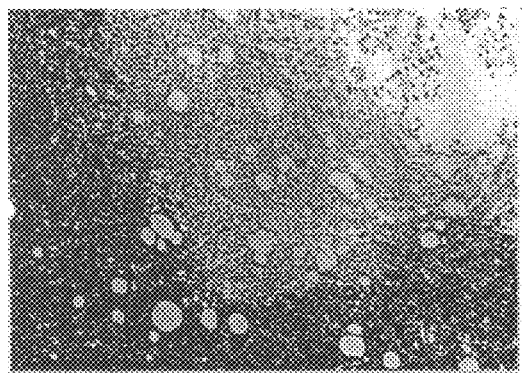
FIG. 1, is a detailed photomicrography of programmed human prostate tumor cell death after H&E staining of PC-3 prostate tumor tissues following immunologically targeting human PC-3 prostate tumors in experimental mice models with garlic extracts containing allicin.
Figure 1:
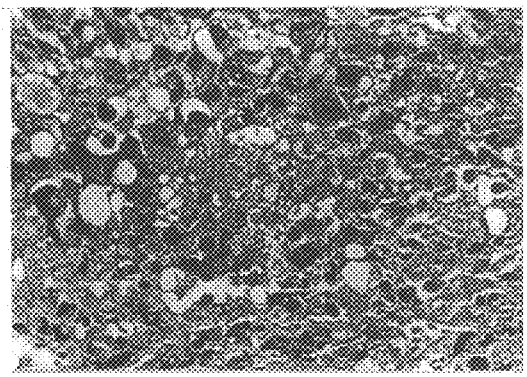
Figure 2:
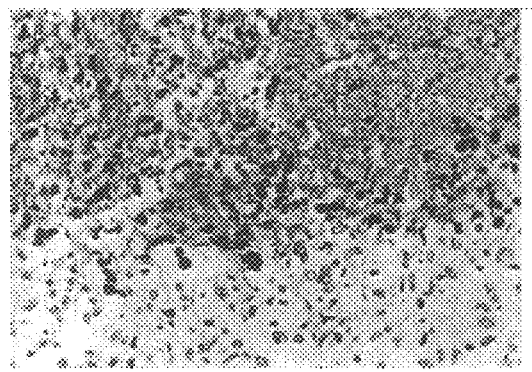
FIG. 2, is a detailed photomicrography of a human PC-3 prostate tumor cell death after processing with both immunologic and tunnel assays with Apotaq Kits following the immunologically targeting of human tumors in experimental mice with garlic extracts containing allicin.
Figure 2:
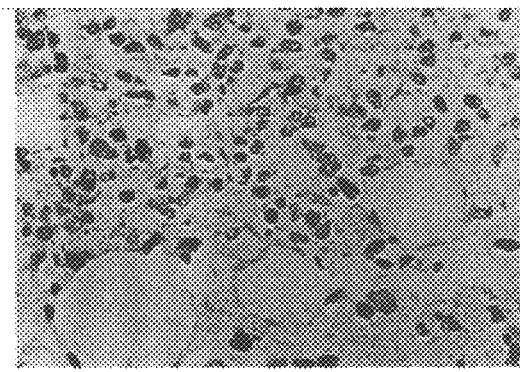

This invention is organized into two parts: 1) describing the chemotherapeutic effects of garlic extracts containing allicin for prostate tumor treatment; and 2) describing the chemotherapeutic effects of garlic extracts containing allicin for treatment of bladder tumors.

The inventors grounded 500 kg of fresh garlic and mixed the grounded garlic with an equal amount of vegetable oil and left the mixture for 4 to 6 days. They then separated and purified the garlic extract by either column chromatography or preparative column chromatography after removing water moisture by adding anhydrated sodium sulfate ($1/10$ of the original starting material). The purified garlic extracts containing allicin were clear yellow liquids with a strong garlic odor and possessed a specific gravity of 0.906~0.913 and an acidity of 1.0. The saponification number was 163~180, the iodine number ranged from 94~106, and the allicin content was greater than 0.1%. The garlic extracts used for the experimental mice were repeatedly tested for microbial contamination such as *E. coli*, Staphylococcus, Streptococcus, and Salmonella prior to animal treatment. In addition, the garlic extracts were tested for heavy metals as well as pesticide contaminants such as BHC, DDT, Aldrin, Dieldrin, and Dieldrin. Only garlic extracts contaminated with less than 30 ppm heavy metals, and with less than 0.01 ppm pesticide residue were used.

If necessary the concentration of allicin in the garlic extracts can be adjusted by adding the appropriate amount of pharmaceutical formulation used for antibacterial use. Allicin concentrations are adjusted to optimize the formulation, frequency of dosing, and interval of dosing for the treatment of prostatic or bladder cancer patients. The extent of the adjustment was based on the patient's age, body weight, the clinical status of the cancers, and the patient's general health.

The formulation of garlic extract containing allicin, as described technically in the preceding statements, is directly administered using syringes into prostatic and bladder tumors as guided by CT scan, MRI or biosonargram imaging. Direct administration of allicin into tumor masses shows not only induced programmed tumor cell death and inhibited tumor cell growth, but also tumor regression by the activation of immune functions. Furthermore, these kind of therapeutic actions are attributed to the interaction between cancer-cell antigens and allicin as a biological response modifier which operates by either direct or indirect action on the immune system. Furthermore, either prostatic or bladder tumor growth rates are closely dependent on angiogenesis, and if angiogenesis is inhibited effectively, prostatic and bladder tumor growth will be effectively inhibited. Even healthy subjects, who have a higher risk of prostate cancer due to aging, race (black), and/or heredity may be given prophylactic administration of garlic extracts containing allicin directly adjacent to the prostate gland potentially prevent prostatic tumors. The injection of garlic extracts containing allicin to areas adjacent to the prostate gland can be easily performed in the ambulatory care unit without any side effects such as bleeding or pain. The injected garlic extract containing allicin will interact with cells adjacent to the prostate gland and will also modulate immune functions to prevent prostatic tumor formation by blocking the transformation process of normal prostatic cells to prostatic tumor cells.

Likewise, a direct administration of garlic extracts containing allicin as a cancer preventive agent can effectively inhibit bladder cancer development among elderly high risk adult males and females with long term smoking habits and among the high risk occupational group of workers in the leather industry, without significant side effects such as hemorrhaging or pain.

The possible mechanism(s) of the cancer preventive action is as previously described.

Direct administration of garlic extracts containing allicin to tumors may be highly effective as a new chemotherapeutic agent to treat prostatic and bladder cancers partly due to anti-angiogenesis, the inhibition of the growth of microvessels that supply the essential nutrition to growing tumor tissues. The direct administration of garlic extracts containing allicin into vessels of tumors can possibly inhibit the growth of microvessls to tumor tissue masses. Jugular vein angiography can easily be used to monitor vessel size, location, and vessel numbers in tumors by using a microvessel angiography during the direct injection of garlic extracts containing allicin into prostatic or bladder cancer patients to possibly attain a highly effective therapeutic response without any serious side effects to normal tissue adjacent to that of the tumor tissues. Furthermore, the direct administration of garlic extracts containing allicin directly into tumor vessels can directly regulate local cellular immunologic response along with the activation of humoral immune response, which in turn immediately leads to programmed endothelial cell deaths in both prostatic and bladder tumor masses thereby blocking tumor growth.

Garlic is a widely used food in general and is not only cheap but also, unlike most drugs, garlic extracts containing allicin do not cause any side effects. Thus, it is ideal for continuous therapy by oral route, for the continued maintenance of stimulated immune response and for the prevention of prostatic and bladder tumor formations. The oral route formulation of garlic extracts containing allicin is similar to that of other oral drug formulations. It is also possible to formulate the extracts to preserve the stability of allicin since continuous oral administration is a very effective mode of preventing prostatic and bladder tumor formations. This is one of the keys to this invention.

For the investigation of garlic extracts containing allicin against prostatic tumor animal models, the test garlic extracts used were without heavy metals, pesticide, BHC, DDT, Aldrin, Dieldrin and Endrin or microbial contaminations, general bacteria, *E. coli*, Streptococci, Staphyosocci, and Salmonella, etc.

This invention relates to garlic extracts that can be mixed with binding inert materials to manufacture the capsules, beads, and tablets.

The following examples are presented below to better describe the invention's purpose, the invention is not limited to the experimental results.

EXAMPLE 1

Investigation of Anticancer Effects Against Human Prostate Tumors

To establish human prostatic tumor animal models, both sides of the abdomen of athymic nude mice (nv/nv) were inoculated with 1×106 hormone-independent PC-3 human prostatic tumor cells grown in T-medium. Experimental animal groups consisted of both treatment and control group(s). Treatment Group (1) was given direct injection of garlic extracts containing allicin into the tumor transplanted site(s). The treatment group consisted of 15 mice with a total of 30 prostatic tumor sites and were treated starting the day after the tumor transplantation, once weekly for 5 weeks with 5 mg garlic extract containing 0.03 mg allicin (the total dose received was per mouse 25 mg garlic extracts containing 0.15 allicin). In contrast, Control Group (II) consisted of 8 athymic nude mice that were directly injected with saline into the tumor sites. Tumor sizes were measured weekly using a tumor caliper. In the treatment group, allicin modulated immunotherapeutic effects were evaluated with respect to tumor incidence, tumor growth rates, histopathologic evaluation and the duration of animal survival. These results can be statistically analyzed to determine any significant differences between the control group and the treatment group.

As shown in Table 1, Experimental Group I, which was given weekly immunotherapy with garlic extracts with allicin for 5 weeks starting the day after xenografting of human prostatic tumor cell lines, showed only a 13.3% incidence of prostatic tumors. Thus, 5 weeks of immunotherapy with garlic extracts was statistically (fishers exact test) significant ($p<0.01$) as compared to that of the control group. Furthermore, the tumor sizes and the tumor volumes in treatment Group I are significantly reduced as compared to that of the control Group II as determined by the Mann-Whitney U nonparametric test ($P<0.01$). The results clearly demostrate that immunotherapy with garlic extracts containing allicin effectively prevented tumor appearance, tumor growth, and tumor progression in athymic nude mice bearing human prostatic tumor cells.

TABLE 1

The immunotherapeutic effects of garlic extracts containing allicin in athymic nude mice xenograted with hormone-independent human prostatic tumor cell lines (PC-3)

| Experimental groups | Prostatic tumor incidence (day 21) | Prostatic tumor sizes (day 35, mm ± SD) |
| --- | --- | --- |
| Group I (Treatment group) | 4/30 (13.3%) | 190.25 ± 68.89 |
| Group II (Saline control group) | 8/8 (100.0%) | 1209.75 ± 217.1 |

The observations of tumor incidence, tumor sizes, and tumor growth rates shown in Tables 1 & 2 were confirmed by microscopic histopathology as well as immunohistochemistry. These results show that the immunotherapeutic targeting of prostate cancers with garlic extracts containing allicin is a very effective way to induce programmed prostatic tumor cell death.

EXAMPLE 2

Investigation of Anticancer Effects Against Human Bladder Cancers

Experimental Example 1

To evaluate the anticancer effects against human bladder tumors, 1×105 mouse transitional epithelial bladder tumor cell lines, MBT-2 cells were transplanted onto the abdominal region of 24 female mice of C3H/He mouse strain. The experimental mice were split into two groups, each consisting of 12 mice. A day after tumor cell inoculation, the mice of Experimental Group 1 were treated directly into the tumor transplantation site(s) with 5 mg of garlic extracts containing 0.03 mg allicin (total dose received: 25 mg garlic extracts containing 0.15 mg allicin)once per week for 5 weeks. The mice in Experimental Group 2 were given weekly injections of saline and served as a control group. Tumor growth and sizes were determined weekly using a tumor caliper. The immunotherapeutic effects of allicin were evaluated by evaluating tumor incidence, tumor growth rates, histopathology of tumors, and the survival rates of tumor bearing mice. The final results were statistically analyzed.

As shown in the Table 2, the results demonstrate that after 5 weeks of treatment with garlic extracts containing allicin only 2 out of 12 mice in Experimental Group 1 showed bladder tumors (16.7%), while all control mice in the Experimental Group 2 showed tumor growth (100%). Thus, the results clearly demonstrate that the chemopreventive effects of garlic extracts containing allicin significantly reduce the incidence of bladder tumors. The Fishers exact test showed a significant difference between the control and the test groups ($p<0.05$). Furthermore, none of the mice in Experimental Group 1 which were treated with garlic extracts containing allicin for the 5-week duration died due to treatment related toxicity.

TABLE 2

The prevention of bladder tumor formation by the imunotherapeutic effects of garlic extracts containing allicin in MBT-2 mouse bladder tumor bearing mice

| Experimental groups | Bladder tumor incidence (Day 28) | Survival of mice (After treatment of garlic extracts) |
| --- | --- | --- |
| Group I Z (Treatment group) | 2/12 (16.7%) | 0/12 (0.0%) |
| Group II (Saline control group) | 12/12 (100%) | 0/12 (0.0%) |

Experimental Example 2

Another experiment that consisted of 24 female mice of C3H/He mouse strain were transplanted with 1×105 cultured transitional bladder epithelial cell tumors, MBT-2 cell lines. Seven days after the tumor transplants, when bladder tumor sizes ranged from 55–65 mm$^3$ in all 24 mice, the mice were divided into two experimental groups, each group consisted of 12 mice. The mice in Experimental Group 1 were treated once a week for 5 weeks duration with 5 mg of garlic extracts containing 0.03 mg allicin by direct injection into the tumor sites (Total dose: 25 mg garlic extracts containing 0.15 mg allicin). The mice in Experimental Group 2 were treated the same way but with saline. Subsequently, the tumor sizes were measured weekly with a tumor caliper to assess the immunotherapeutic effects of allicin with respect to tumor incidence, growth rates, histopathologic examination, and the animal survival. The results of the experiment in table 3 shows that 35 days after tumor cell transplants, the average tumor volumes in the allicin treated group was 1534.8±562 mm$^3$, however, that of the control group was 5120.6±812.5 mm$^3$. Therefore, it was clearly demonstrated that the average bladder tumor sizes in the allicin treatment group were significantly reduced by immunotherapeutic effects. The statistical differences between the treated group versus that of the control group was highly significant (Mann-Whitney nonparametric test, $p<0.05$). It is clearly evident from this experiment that the growth of bladder tumors in these experimental mice were significantly inhibited by garlic extracts containing allicin. Furthermore, the survival of the mice in Experimental Group 1 which were treated with the immunotherapeutic effects of garlic extracts containing allicin was significantly greater than that of control group.

TABLE 3

The immunotherapeutic effects of garlic extracts containing allicin MBT-2 bladder tumor bearing mice

| Experimental groups | Bladder tumor size (mm3) (Day 35, Mean ± SD) | Survival of mice (Day 42) |
| --- | --- | --- |
| Group I (Treatment group) | 1534.8 ± 552.4 | 3/12 (25%) |
| Group II (Saline control group) | 5120.6 ± 812.5 | 1/12 (8.3%) |

Figure 3:
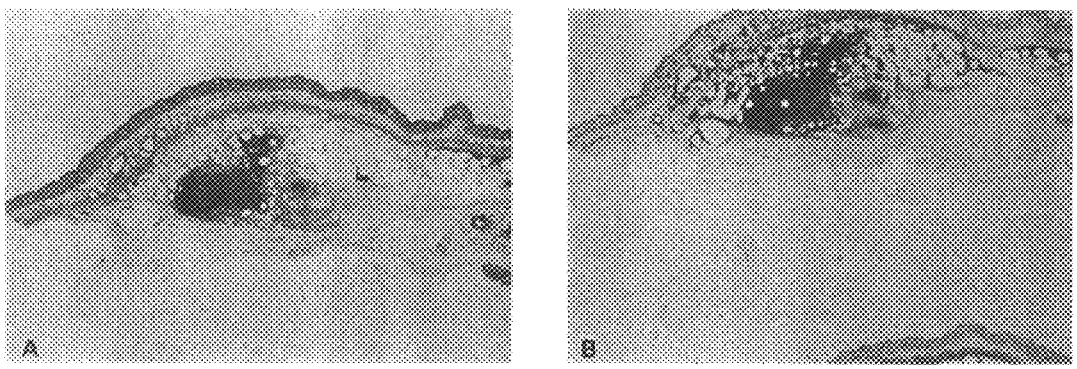
FIG. 3 shows a detailed photomicrography of programmed cell death of most of the bladder tumor cells with tunnel assays with Apotaq kits 2-weeks following immunologically targeted treatment of MB-2 bladder tumor bearing mice with garlic extracts containing allicin.
Figure 4:
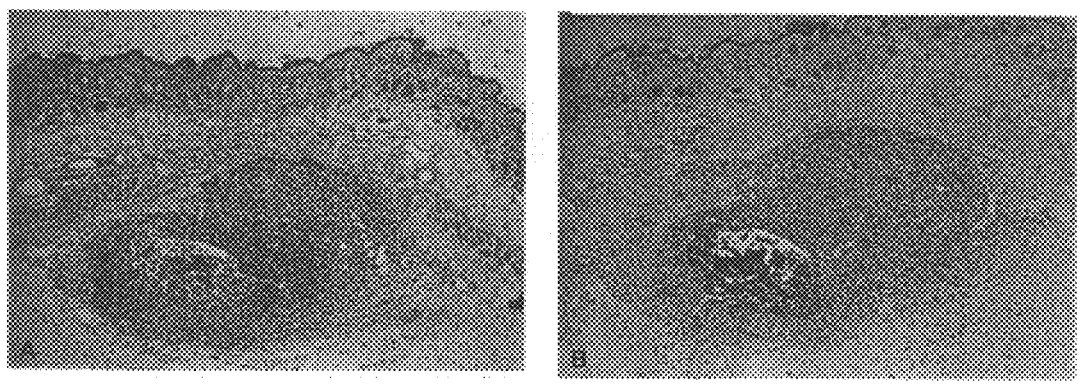
FIG. 4 shows programmed bladder tumor cell[s] death evidenced by immunohistochemical and Tunnel assay with Apotaq kits after 2-weeks of continued immunologically targeting of bladder tumor bearing mice with garlic extracts containing allicin.

After sacrificing mice with transplanted bladder tumors, the immunotherapeutic effects of garlic extracts containing allicin were evaluated by immunohistochemistry and microscopic histopathology. FIGS. 3 and 4, clearly demonstrated programmed cell death accompanied by tumor regression.

As explained by the experimental results, this invention describes and demonstrates that garlic extracts containing allicin, diallyl disulfide, diallyl trisulfide, and others, etc. possess both preventive and chemotherapeutic effects against human prostate and bladder tumors and thus, this invention is a very useful invention for the biopharmaceutical industry.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A chemopreventive and chemotherapeutic composition for treating prostate and bladder cancer, comprising:

a chemopreventively and chemotheropeutically effective amount of a garlic extract comprising allicin, diallyl disulfide and diallyl trisulfide, wherein the garlic extract is prepared by adding garlic to vegetable oil to form a garlic and vegetable oil composition, removing water moisture from the garlic and vegetable oil composition by adding anhydrous sodium sulfate, and separating the garlic extract from the garlic and vegetable oil composition and wherein the garlic and vegetable oil composition is aged for 4 to 6 days before removing the water moisture and the garlic extract has a specific gravity of 0.906 to 0.913, an acidity of 1.0, a saponification number of 163 to 180, and an iodine number from 94 to 106.

2. The chemopreventive and chemotherapeutic composition of claim 1, wherein the allicin content is greater than 0.1% weight.

3. The chemopreventive and chemotherapeutic composition of claim 1, wherein the garlic extract is separated from the garlic and vegetable oil composition using a column chromatograph.

* * * * *